US006641823B2

(12) United States Patent
Piot et al.

(10) Patent No.: US 6,641,823 B2
(45) Date of Patent: Nov. 4, 2003

(54) MAKE-UP COMPOSITION FOR THE SKIN

(75) Inventors: Bertrand Piot, Paris (FR); Nathalie Collin, Sceaux (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/977,279

(22) Filed: Oct. 16, 2001

(65) Prior Publication Data

US 2002/0102283 A1 Aug. 1, 2002

(30) Foreign Application Priority Data

Oct. 16, 2000 (FR) .............................. 00 13240

(51) Int. Cl.⁷ .............................. A61K 6/00; A61K 7/00; A61K 7/021
(52) U.S. Cl. ...................... 424/401; 424/78.03; 424/63; 514/772.3
(58) Field of Search ............................. 424/400, 78.03, 424/401, 70.7, 64, 63

(56) References Cited

U.S. PATENT DOCUMENTS

| 3,734,874 A | 5/1973 | Kibler et al. ............ 260/29.2 E |
| 4,233,196 A | 11/1980 | Sublett .................. 260/29.2 N |
| 4,304,901 A | 12/1981 | O'Neill et al. .............. 528/290 |
| 4,423,031 A | 12/1983 | Murui et al. ................... 424/63 |
| 5,261,426 A | 11/1993 | Kellett et al. ................ 132/108 |
| 5,534,247 A * | 7/1996 | Franjac et al. ............. 424/70.7 |
| 5,993,784 A | 11/1999 | Hill .............................. 424/49 |

FOREIGN PATENT DOCUMENTS

| FR | 1 504 440 | 12/1967 |
| WO | WO 98/30195 | 7/1998 |
| WO | WO00/33806 | 6/2000 |

OTHER PUBLICATIONS

English language Derwent Abstract of FR 1 504 440, Dec. 8, 1967.

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

A make-up cosmetic composition for the skin comprising, in a cosmetically acceptable aqueous medium, at least one film-forming polymer, at least one nonionic surfactant, and at least one pulverulent coloring matter, wherein said at least one nonionic surfactant is chosen from polyethylene glycol/polypropylene glycol/polyethylene glycol triblock polycondensates. The composition makes it possible to obtain a make-up for the skin having good covering power and which is tolerated by sensitive skins and/or eyes.

29 Claims, No Drawings

MAKE-UP COMPOSITION FOR THE SKIN

The subject of the present invention is a cosmetic composition comprising, in an aqueous medium, at least one film-forming polymer, at least one nonionic surfactant, and at least one pulverulent coloring matter, intended as make-up for the skin, including the lips. The invention also relates to a method for the application of make-up to the skin, in certain embodiments the skin of human beings. The composition may be provided in the form of an eyeliner, a product for the lips or a make-up product for the body or the face.

Make-up compositions for the skin, in certain embodiments eyeliners, containing, in an aqueous medium, film-forming polymers and pigments are known, for example, FR-A-1504440 and U.S. Pat. No. 4,423,031. Users desire make-up compositions having good homogeneous coverage, i.e. a composition forming a sufficiently colored make-up film to mask the skin to which make-up has been applied. To obtain homogeneous covering, the pigments should be well dispersed in the aqueous medium without forming agglomerates. To properly disperse the pigments in the aqueous medium for the composition, dispersing surfactants have been used; however, some surfactants irritant sensitive skin. Make-up compositions containing these surfactants are not well tolerated by users. Thus, an eyeliner applied to the edge of the eyelids can cause eye discomfort due to the sensation of prickling or burning at the edge of the eyelids which is caused by the irritating surfactants.

The inventors' research sought to provide a make-up composition for the skin, in certain embodiments for the edge of the eyelids, containing at least one film-forming polymer and at least one pulverulent coloring matter in an aqueous medium, which has good covering properties and is well tolerated by sensitive skins and/or eyes.

The inventors have observed that such a composition could be obtained using at least one nonionic surfactant which is chosen from polyethylene glycol/polypropylene glycol/polyethylene glycol triblock polycondensates. The use of such surfactants makes it possible to obtain good dispersion of the pulverulent coloring matter in the aqueous medium of the composition. The composition, when applied to the skin, forms a make-up exhibiting good homogeneous coverage. This make-up is, moreover, well tolerated and is therefore suitable as make-up for sensitive eyes.

Embodiments of the invention include make-up cosmetic compositions for the skin comprising, in a cosmetically acceptable aqueous medium, at least one film-forming polymer, at least one nonionic surfactant, and at least one pulverulent coloring matter, wherein the at least one nonionic surfactant is chosen from polyethylene glycol/polypropylene glycol/polyethylene glycol triblock polycondensates.

Other embodiments of the invention include methods for the application of make-up to the skin comprising the application, to the skin, of a composition as defined above.

Other embodiments of the invention include methods for the application of make-up to the edge of the eyelids comprising the application, to the edge of the eyelids, of a composition as defined above.

Other embodiments of the invention include uses of a composition as defined above for obtaining a make-up having good coverage and/or which is tolerated by sensitive skins and/or eyes.

Other embodiments of the invention include the use of at least one nonionic surfactant (i.e., polyethylene glycol/polypropylene glycol/polyethylene glycol triblock polycondensates), at least one film-forming polymer and at least one pulverulent coloring matter, in a make-up cosmetic composition for the skin comprising a cosmetically acceptable aqueous medium, for obtaining a make-up having good coverage and/or which is tolerated by sensitive skins and/or eyes.

The expression "cosmetically acceptable aqueous medium" can be understood to mean a medium which is compatible with keratinous materials, in particular the skin.

The aqueous medium of the composition may also comprise at least one water-miscible organic solvent, for example $C_2$–$C_6$ monoalcohols such as ethanol or isopropanol. The water-miscible organic solvent, for example a $C_2$–$C_6$ monoalcohol, may be present in an amount ranging from 0.1% to 20% by weight, relative to the total weight of the composition.

The expression "film-forming polymer" can be understood to mean a polymer which is capable of forming, on its own or in the presence of a film-forming aid, a continuous and adherent film on a support, in particular on the skin.

The at least one film-forming polymer present in the composition according to the invention may be chosen from:
  proteins such as proteins of plant origin like wheat and soyabean proteins; proteins of animal origin like keratins, for example keratin hydrolysates and sulphonic keratins;
  anionic, cationic, amphoteric and nonionic polymers of chitin and chitosan;
  cellulose polymers for example hydroxyethyl cellulose, hydroxypropyl cellulose, methyl cellulose, ethyl hydroxyethyl cellulose, carboxymethyl cellulose, and the quaternized derivatives of cellulose;
  acrylic polymers and copolymers, for example polyacrylates and polymethacrylates;
  vinyl polymers, such as polyvinylpyrrolidones, copolymers of methyl vinyl ether and maleic anhydride, the copolymer of vinyl acetate and crotonic acid, copolymers of vinylpyrrolidone and vinyl acetate; copolymers of vinylpyrrolidone and caprolactam; polyvinyl alcohol;
  polyesters, in some embodiments anionic polyester and/or polyester amide polymers, which are in certain embodiments dispersible in water, comprising monomers carrying a functional group: —$SO_3M$, with M chosen from hydrogen atoms, ammonium ions ($NH_4^+$) or metal ions, for example $Na^+$, $Li^+$, $K+$, $Mg^{2+}$, $Ca^{2+}$, $Cu^{2+}$, $Fe^{2+}$, and $Fe^{3+}$ ions. Appropriate polymers include those described in U.S. Pat. Nos. 3,734,874; 4,233,196; and 4,304,901. In certain embodiments, film-forming polyester polymers based on at least one dicarboxylic acid, at least one diol and at least one bifunctional aromatic monomer carrying, in addition, a group —$SO_3M$ as described above are chosen from;
  a polyester having a fatty chain, a polyamide and an epoxy ester resin;
  a polyurethane polymer, in certain embodiments anionic, cationic, nonionic and amphoteric polyurethanes, polyurethane-acrylics, polyurethane-polyvinylpyrrolidones, polyester-polyurethanes, polyether-polyurethanes, polyureas, polyurea/polyurethanes;
  an optionally modified polymer of natural origin chosen from at least one of:
    gum arabic, guar gum, xanthan derivatives, karaya gum;
    alginates and carrageenans;

glycoaminoglycans, hyaluronic acid, and its derivatives;

shellac resin, sandarac gum, dammars, elemis, copals; deoxyribonucleic acid;

mucopolysaccharides such as hyaluronic acid, chondroitin sulphates, and mixtures thereof.

In certain embodiments, the at least one film-forming polymer may be solubilized or dispersed in the aqueous medium of the composition.

The expression "solubilized in the aqueous medium" is understood to mean a polymer soluble in water or in the mixture of water and of solvent as defined above.

The expression "dispersed in the aqueous medium" is understood to mean a polymer insoluble in water or the mixture of water and solvents as defined above, provided in the form of solid particles in dispersion in the aqueous medium. Such dispersions may in some embodiments be a latex, i.e., a dispersion obtained by polymerization in emulsion, or in other embodiments a pseudolatex, i.e., a dispersion obtained by dispersing the polymer already synthesized. Techniques for preparing these dispersions are well understood by those skilled in the art.

In certain embodiments, the at least one film-forming polymer may be present in the composition according to the invention in an amount ranging from 0.5% to 20% by weight, relative to the total weight of the composition, and in certain embodiments ranging from 1% to 15% by weight, relative to the total weight of the composition.

The at least one nonionic surfactant present in the composition according to the invention is chosen from polyethylene glycol/polypropylene glycol/polyethylene glycol triblock polycondensates. This triblock polycondensate has, for example, the following chemical structure:

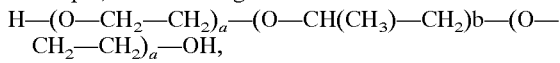

in which a ranges from 2 to 120, and b ranges from 1 to 100.

The at least one nonionic surfactant in some embodiments has a weight-average molecular weight ranging from 1000 to 15,000, and in certain embodiments ranging from 2000 to 13,000.

In some embodiments, the at least one surfactant has a cloud temperature, at 10 g/l in distilled water, greater than or equal to 20° C., and in certain embodiments greater than or equal to 60° C. The cloud temperature is measured according to the ISO 1065 standard.

In certain embodiments, the at least one nonionic surfactant is chosen from the polyethylene glycol/polypropylene glycol/polyethylene glycol triblock polycondensates sold under the names "SYNPERONIC" such as "SYNPERONIC PE/L44" and "SYNPERONIC PE/F127" by the company ICI.

The at least one nonionic surfactant may be present in the composition according to the invention in an amount effective for dispersing the pulverulent coloring matter in the aqueous medium. In some embodiments, the amount of nonionic surfactant may range from 0.1% to 15% by weight, relative to the total weight of the composition, and in certain embodiments from 1% to 10% by weight relative to the total weight of the composition.

The composition of the invention comprises one or more type(s) of pulverulent coloring matter which may be chosen from pigments, pearlescent agents normally used in cosmetic compositions and mixtures thereof.

The pigments may be white or colored, inorganic and/or organic, interferential or otherwise. In certain embodiments, the inorganic pigments may be chosen from at least one of titanium dioxide; optionally surface-treated zirconium or cerium oxide, and zinc, iron or chromium oxides; manganese violet, ultramarine blue, chromium hydrate and ferric blue. In certain other embodiments, the organic pigments may be chosen from at least one of carbon black, pigments of the D & C type, and lakes based on cochineal carmine, barium, strontium, calcium or aluminum.

The pearlescent pigments may be chosen from at least one white pearlescent pigment such as mica coated with titanium or bismuth oxychloride, colored pearlescent pigments such as mica-titanium with iron oxides, mica-titanium with in certain embodiments, ferric blue or chromium oxide, mica-titanium with an organic pigment of the abovementioned type, or pearlescent pigment based on bismuth oxychloride.

In some embodiments, at least one pulverulent coloring matter may be present in the composition according to the invention in an amount ranging from 0.1% to 40% by weight, relative to the total weight of the composition, and in certain embodiments from 0.5% to 30% by weight, relative to the total weight of the composition.

In certain embodiments, the composition according to the invention may contain, in addition, at least one glycol to allow good wetting of the pigments, i.e., to facilitate their use and their homogeneous dispersion in the aqueous medium of the composition. The glycol also makes it possible to plasticize the polymer film i.e., to make the film more supple. Glycol also allows good wetting of the skin, facilitating spreading of the composition on the skin. In the present application, the term glycol is understood to mean a diol comprising from 2 to 8, such as from 2 to 4, carbon atoms.

In certain embodiments, the at least one glycol may be chosen from propylene glycols, ethylene glycols, 1,3-butylene glycols, and dipropylene glycols.

In some embodiments, the at least one glycol may be present in the composition in an amount ranging from 0.1% to 30% by weight, relative to the total weight of the composition, such as from 5% to 20% by weight, relative to the total weight of the composition.

In some embodiments of the composition according to the invention, water may be present in an amount ranging from 10% to 90% by weight, relative to the total weight of the composition, and in certain embodiments ranging from 30% to 50% by weight, relative to the total weight of the composition.

In some embodiments of the composition according to the invention, the composition may additionally comprise at least one filler which may be chosen from those well known to one skilled in the art and commonly used in cosmetic compositions. Such fillers may be chosen from, for example:

talc which in certain embodiments is a magnesium silicate hydrate used in the form of particles generally of less than 40 microns, mica which in certain embodiments are aluminosilicates of varied compositions provided in the form of scales having sizes of 2 to 200 microns, and in certain other embodiments having sizes of 5 to 70 microns; and a thickness of between 0.1 and 5 microns, and in certain other embodiments a thickness of between 0.2 and 3 microns. This mica in some embodiments may be of natural origin such as muscovite, margarite, roscoelite, lipidolite, biotite, or of synthetic origin, starch, in certain embodiments rice starch, kaolin which is an aluminum silicate hydrate which exists in the form of particles of isotropic form having sizes generally of less than 30 microns, zinc and titanium oxides generally used in the form of particles having sizes not exceeding a few microns, calcium carbonate, magnesium carbonate, or hydrocarbonate, microcrystalline cellulose, silica, powders of synthetic polymers such as polyethylene, polyesters (polyethylene isophthalate or terephthalate), polyamides such as those sold under the trade name "Nylon" or "Teflon," and silicone powders.

In some embodiments, the composition according to the invention may comprise at least one cosmetic additive chosen from thickening agents, preservatives, perfumes, water-soluble colorants, vitamins, moisturizing agents, emollients, sunscreens, sequestrants, alkalinizing and acidifying agents, plasticizers.

It would be readily apparent to the skilled artisan to choose additive compounds, and/or their quantity, so that the advantageous properties of the composition according to the invention are not, or are not substantially, impaired by the addition envisaged.

The composition according to the invention may be prepared according to the customary methods in the fields considered.

The invention is illustrated in greater detail in the following examples.

EXAMPLE 1

An eyeliner having the following composition was prepared:

| | |
|---|---|
| Vinylpyrrolidone/vinyl acetate copolymer (70/30) in solution at 50% in ethanol sold under the name "LUVISKOL VA 73 E" by the company BASF | 10 g |
| Ethylene oxide/propylene oxide/ethylene oxide condensate (11/21/1) sold under the name "SYNPERONIC PE/L 44" by the company ICI | 6 g |
| Black iron oxide | 20 g |
| Propylene glycol | 15 g |
| Ethanol | 7 g |
| Preservatives | qs |
| Water | qs 100 g |

The liner could be easily applied to the edge of the eyelids and formed a make-up film having good coverage. Moreover, the make-up obtained was well tolerated by people having sensitive eyes.

EXAMPLE 2

An eyeliner having the following composition was prepared:

| | |
|---|---|
| Vinylpyrrolidone/vinyl acetate copolymer (70/30) in solution at 50% in ethanol sold under the name "LUVISKOL VA 73 E" by the company BASF | 6 g |
| Ethylene oxide/propylene oxide/ethylene oxide condensate (98/67/98) sold under the name "SYNPERONIC PE/F 127" by the company ICI | 5 g |
| Black iron oxide | 20 g |
| Propylene glycol | 15 g |
| Ethanol | 7 g |
| Aluminum and magnesium silicate | 1 g |
| Preservatives | qs |
| Water | qs 100 g |

After application to the edge of the eyelids, this liner formed a make-up film having good coverage. The make-up obtained was also well tolerated by people having sensitive eyes.

What is claimed is:

1. A make-up cosmetic composition for the skin comprising, in a cosmetically acceptable aqueous medium, at least one film-forming polymer, at least one nonionic surfactant, and at least one pulverulent coloring matter, wherein said at least one nonionic surfactant is chosen from polyethylene glycol/polypropylene glycol/polyethylene glycol triblock polycondensates.

2. A make-up cosmetic composition according to claim 1, wherein the at least one nonionic surfactant has a weight-average molecular weight ranging from 1000 to 15,000.

3. A make-up cosmetic composition according to claim 2, wherein said at least one nonionic surfactant has a weight-average molecular weight ranging from 2000 to 13,000.

4. A make-up cosmetic composition according to claim 1, wherein the at least one nonionic surfactant has a cloud temperature, at 10 g/l in distilled water, greater than or equal to 20° C.

5. A make-up cosmetic composition according to claim 4, wherein the at least one nonionic surfactant has a cloud temperature, at 10 g/l in distilled water, greater than or equal to 60° C.

6. A make-up cosmetic composition according to claim 1, wherein the at least one nonionic surfactant is present in an amount ranging from 0.1% to 15% by weight, relative to the total weight of the composition.

7. A make-up cosmetic composition according to claim 6, wherein the at least one nonionic surfactant is present in an amount ranging from 1% to 10% by weight.

8. A make-up cosmetic composition according to claim 1, wherein the at least one film-forming polymer is chosen from keratin polymers, chitin and chitosan polymers, cellulosic polymers, acrylic polymers, acrylic copolymers, vinyl polymers, polyesters, polyamides, epoxy ester resins, polyurethanes, and optionally modified polymers of natural origin.

9. A make-up cosmetic composition according to claim 1, wherein the at least one film-forming polymer is chosen from polyvinylpyrrolidones, copolymers of methyl vinyl ether and maleic anhydride, copolymers of vinyl acetate and crotonic acid, copolymers of vinylpyrrolidone and vinyl acetate; copolymers of vinylpyrrolidone and caprolactam; polyvinyl alcohols; hydroxethyl celluloses, hydroxypropyl celluloses, methyl celluloses, ethyl hydroxyethyl celluloses, carboxymethyl celluloses, quaternized derivatives of cellulose; polyesters; polyurethane-acrylics, polyurethane-polyvinylpyrrolidones, polyester-polyurethanes, polyether-polyurethanes, polyureas, polyurea/polyurethanes; gum arabics, guar gums, xanthan derivatives, karaya gums; alginates, carrageenans; glycoaminoglycans, hyaluronic acid and its derivatives; shellac resins, sandarac gums, dammars, elemis, copals; deoxyribonucleic acids; and mucopolysaccharides.

10. A make-up cosmetic composition according to claim 9 wherein the polyesters are selected from anionic polyesters and polyester amide polymers comprising monomeric residues carrying an —SO$_3$M functional group, wherein M is chosen from hydrogen, ammonium ions NH$_4^+$ and metal ions.

11. A make-up cosmetic composition according to claim 1, wherein the at least one film-forming polymer is chosen from copolymers of vinylpyrrolidone and vinyl acetate.

12. A make-up cosmetic composition according to claim 1, wherein the at least one film-forming polymer is present in an amount ranging from 0.5% to 20% by weight, relative to the total weight of the composition.

13. A make-up cosmetic composition according to claim 12, wherein the at least one film-forming polymer is present in an amount ranging from 1% to 15% by weight, relative to the total weight of the composition.

14. A make-up cosmetic composition according to claim 1, wherein the at least one pulverulent coloring matter is chosen from pigments and pearlescent agents.

15. A make-up cosmetic composition according to claim 1, wherein the at least one pulverulent coloring matter is chosen from titanium dioxide, zirconium oxide, cerium oxide, zinc oxide, iron oxide, chromium oxide, manganese violet, ultramarine blue, chromium hydrate and ferric blue, carbon black, lakes based on cochineal carmine, barium, strontium, calcium, and aluminum, mica coated with titanium or bismuth oxychloride, mica-titanium with iron oxides, mica-titanium with ferric blue or chromium oxide, and pearlescent pigments based on bismuth oxychloride.

16. A make-up cosmetic composition according to claim 1, wherein the at least one pulverulent coloring matter is present in an amount ranging from 0.1% to 40% by weight, relative to the total weight of the composition.

17. A make-up cosmetic composition according to claim 16, wherein the at least one pulverulent coloring matter is present in an amount ranging from 0.5% to 30% by weight, relative to the total weight of the composition.

18. A make-up cosmetic composition according to claim 1, further comprising at least one glycol comprising from 2 to 8 carbon atoms.

19. A make-up cosmetic composition according to claim 18, wherein the at least one glycol is chosen from propylene glycol, ethylene glycol, 1,3-butylene glycol, and dipropylene glycol.

20. A make-up cosmetic composition according to claim 18, wherein the at least one glycol is present in an amount ranging from 0.1% to 30% by weight, relative to the total weight of the composition.

21. A make-up cosmetic composition according to claim 20, wherein the at least one glycol is present in an amount ranging from 5% to 20% by weight, relative to the total weight of the composition.

22. A make-up cosmetic composition according to claim 1, further comprising water in an amount ranging from 10% to 90% by weight, relative to the total weight of the composition.

23. A make-up cosmetic composition according to claim 1, further comprising at least one $C_2$–$C_6$ monoalcohol.

24. A make-up cosmetic composition according to claim 23, wherein the at least one $C_2$–$C_6$ monoalcohol is present in an amount ranging from 0.1% to 20% by weight, relative to the total weight of the composition.

25. A make-up cosmetic composition according to claim 1, further comprising at least one cosmetic additive chosen from fillers, thickening agents, preservatives, perfumes, water-soluble colorants, vitamins, moisturizing agents, emollients, sunscreens, sequestrants, alkalinizing and acidifying agents, and plasticizers.

26. An eyeliner, a make-up product for the body or the face, or a product for the lips comprising, in a cosmetically acceptable aqueous medium, at least one film-forming polymer, at least one nonionic surfactant, and at least one pulverulent coloring matter, wherein said at least one nonionic surfactant is chosen from polyethylene glycol/polypropylene glycol/polyethylene glycol triblock polycondensates.

27. An eyeliner comprising, in a cosmetically acceptable aqueous medium, at least one film-forming polymer, at least one nonionic surfactant, and at least one pulverulent coloring matter, wherein said at least one nonionic surfactant is chosen from at least one polyethylene glycol/polypropylene glycol/polyethylene glycol triblock polycondensate.

28. A method for the application of make-up to skin comprising applying to the skin a composition comprising, in a cosmetically acceptable aqueous medium, at least one film-forming polymer, at least one nonionic surfactant, and at least one pulverulent coloring matter, wherein said at least one nonionic surfactant is chosen from polyethylene glycol/polypropylene glycol/polyethylene glycol triblock polycondensates.

29. A method for the application of make-up to the edge of the eyelids comprising applying, to the edge of the eyelids, a composition comprising, in a cosmetically acceptable aqueous medium, at least one film-forming polymer, at least one nonionic surfactant, and at least one pulverulent coloring matter, wherein said at least one nonionic surfactant is chosen from polyethylene glycol/polypropylene glycol/polyethylene glycol triblock polycondensates.

* * * * *